United States Patent [19]

Revici

[11] Patent Number: 4,596,706

[45] Date of Patent: Jun. 24, 1986

[54] METHOD FOR ELIMINATING OR REDUCING THE DESIRE FOR SMOKING

[75] Inventor: Emanuel Revici, New York, N.Y.

[73] Assignee: Elena Avram, New York, N.Y.

[21] Appl. No.: 722,875

[22] Filed: Apr. 12, 1985

[51] Int. Cl.<sup>4</sup> .................. A61K 31/21; A61K 31/045; A61K 31/105; A61K 31/265; A61K 33/04
[52] U.S. Cl. ....................................... 424/10; 424/162; 514/512; 514/513; 514/706; 514/707; 514/724; 514/738; 514/813
[58] Field of Search .................. 424/10, 162; 514/512, 514/513, 706, 707, 724, 738, 810, 812, 813

[56] References Cited

U.S. PATENT DOCUMENTS

| 3,622,676 | 11/1971 | D'Alonza | 424/162 |
| 4,346,082 | 8/1982 | Reveci | 424/162 |
| 4,416,869 | 11/1983 | Reveci | 424/164 |
| 4,512,977 | 4/1985 | Lundy | 424/162 |

*Primary Examiner*—Stanley J. Friedman
*Attorney, Agent, or Firm*—Pennie & Edmonds

[57] ABSTRACT

A method for treating or aiding in the treatment of a tobacco habit or addiction in a human by controlling the craving for tobacco or controlling tobacco withdrawal symptoms which comprises internally administering to said human an effective amount of a compound having an active ingredient containing at least one bivalent negative sulfur to control said craving or said withdrawal symptoms so as to reduce the desire for tobacco.

13 Claims, No Drawings

METHOD FOR ELIMINATING OR REDUCING THE DESIRE FOR SMOKING

TECHNICAL FIELD

The invention relates to a method for eliminating or reducing the desire to smoke through the administration of catabolic sulfur-containing compounds.

DESCRIPTION OF THE PRIOR ART

Sulfurized polyunsaturated oils, or sulfurized oils are disclosed in a book entitled RESEARCH IN PHYSIOPATHOLOGY AS BASIS OF GUIDED CHEMOTHERAPY by Emanual Revici, M.D., published by D. Van Nostrand Co., Inc., 1961, pages 334 and 335. A method of preparing sulfurized polyunsaturated oils referred to in the book as hydro persulfides is set forth in Note 7, page 711 of the book. This book does not disclose however, the use of these sulfurized compounds for preventing or reducing the desire for smoking tobacco as claimed herein. Further, U.S. Pat. No. 4,416,869 discloses a method for preventing or reducing the desire for smoking tobacco in humans by the internal administration of a composition produced by heating cetain allylically unsaturated compounds which are sufficient to substantially increase the peroxide titer. The incorporation of sulfur into the composition during this heating process has been found to be particularly advantageous. This patent is expressly incorporated herein by reference.

Applicant has now discovered that a number of additional compounds are effective for eliminating or reducing the desire for smoking.

SUMMARY OF THE INVENTION

The invention relates to a method for treating or aiding in the treatment of a tobacco habit or addiction in a human by controlling the craving for tobacco or by controlling tobacco withdrawal symptoms by internally administering a compound with an active ingredient containing at least one bivalent negative sulfur in an amount effective to control the craving or the withdrawal symptoms.

The most clinically effective anti-smoking compounds for use as an active ingredient are hydropersulfides, alkyl sulfides, colloidal sulfur, organic thio compounds or their pharmaceutically acceptable salts. The most effective thio compounds have proven to be thioglycerols, thioglycols or their pharmaceutically acceptable salts.

These compounds are amenable to oral administration into the human body by mixing the active ingredient with suitable binders and bulking materials and placing an amount of the active material which is equal to a therapeutic dosage level into a pharmaceutical capsule.

The preferred theraputic dosage level is 100 milligrams of the active ingredient and the subject should be instructed to ingest a sufficient number of capsules so as to effect a cessation or reduction in his desire to smoke. The active ingredient may also be administered however, by means of an injection, which allows the sulfur compound to work faster initally. The most clinically effective active ingredient is ethylene trithiocarbonate, thioglycerols, and thioglycol.

DETAILED DESCRIPTION OF THE PREFERRED EMBODIMENTS

It is desirable to have a technique for treating or aiding in the treatment of the tobacco habit or addiction in a human by means of a method for controlling the craving for tobacco and/or by reducing or controlling the symptoms of withdrawal. The invention disclosed herein relates to such methods of treatment.

Testing of the products produced by tobacco smoking shows them to possess, in general, a manifest anabolic action. These studies have concerned the fluorescence of the products found in the tobacco smoke and have disclosed the presence of carcinogenic agents which emit energy. Applicant has discovered that the administration of catabolic agents to a human subject, which agents are antagonistic to the anabolic effects of tobacco by-products, is an extremely satisfactory technique for counteracting the subject's desire to smoke.

The applicant has also discovered that certain catabolic agents, especially active at higher levels of the body organization, are more specifically active than others against the physiological changes induced by smoking tobacco. The preferred catabolic agents for performing this function are bivalent negative sulfur compounds which experimentation has shown to be most efficacious. The following specific compounds have been found to be particularly effective in clinical tests for eliminating or reducing the desire for smoking: hydropersulfides, alkyl sulfides, colloidal sulfur and organic thio products, which include but is not limited to thioglycerols and thioglycols, or other pharmaceutically acceptable salts. Applicant has found that the best results are obtained through the use of the thioglycols thisglycerols and, specifically, ethylene trithiocarbonate.

As an alternate embodiment of the present invention, the compounds disclosed herein, may also be mixed with the compounds disclosed in U.S. Pat. No. 4,416,869.

The method of administration for these compounds may be either oral or parenteral and the intended effect, that of diminishing the subject's desire to smoke, may be obtained even after only one of two administrations of these agents. For purpose of the preferred oral note of administration, the active material may be mixed with binders and bulking agents and therapeutic dosages such as 100 milligrams, may be placed in pharmaceutical capsule for dispensing to a subject.

The dosage prescribed to a patient will, of course, vary depending upon the particular patient and the number of cigarettes being smoked per day. In general a daily dosage should consist of about 3–5 capsules containing 100 mg. each of the active ingredient for the first three days after which the dosage level should be progressively reduced in accordance with the subject's reduced desire to smoke. As noted, however, smoking patterns vary and a heavy smoker may require as many as eight capsules per day for the first three days which could then be reduced to 3–4 capsules per day for the next four days. This is generally sufficient to eliminate or reduce a smoker's desire or need for tobacco. A single course of treatment may retain its effect for months but the smoker may also be provided with a supply of the capsules in case the desire for tobacco returns.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

I claim:

1. A method for treating or aiding in the treatment of a tobacco habit or an addiction in a human by controlling the craving for tobacco or controlling tobacco withdrawal symptoms which comprises internally administering to said human an effective amount of ethylene trithiocarbonate, colloidal sulfur, or one of their pharmaceutically acceptable salts to control said craving or said withdrawal symptoms so as to reduce the desire for tobacco.

2. The method of claim 1 wherein the active ingredient is administered by injection.

3. The method of claim 1 wherein the active ingredient is administered orally.

4. The method of claim 1 wherein the active ingredient is mixed with suitable binders or bulking materials and an amount of the mixture equal to a therapeutic dosage level of the active ingredient is then enclosed within a pharmaceutical capsule.

5. The method of claim 4 wherein the theraputic dosage level is about 100 milligrams of the active ingredient per capsule.

6. The method of claim 5 wherein a sufficient number of pharmaceutical capsules are administered to reduce or eliminate a subject's desire to smoke.

7. A method for treating or aiding in the treatment of a tobacco habit or addiction in a human by controlling the craving for tobacco or controlling tobacco withdrawal symptoms which comprises internally administering to said human an effective amount of ethylene tri thiocarbonate to control said craving or said withdrawal symptoms.

8. A method for treating or aiding in the treatment of a tobacco habit or addiction in a human by controlling the craving for tobacco or controlling tobacco withdrawal symptoms which comprises orally administering to said human a sufficient number of pharmaceutical capsules each containing about 100 milligrams of colloidal sulfur or its pharmaceutically acceptable salts.

9. A method for treating or aiding in the treatment of a tobacco habit or addiction in a human by controlling the craving for tobacco or controlling tobacco withdrawal symptoms which comprises orally administering to said human a sufficient number of pharmaceutical capsules each containing about 100 milligrams of ethylene trithiocarbonate.

10. The method of claim 6 wherein 3–5 capsules are administered daily to said human.

11. The method of claim 8 wherein 3–5 capsules are administered daily to said human.

12. The method of claim 9 wherein 3–5 capsules are administered daily to said human.

13. A method for treating or aiding in the treatment of a tobacco habit or an addiction in a human by controlling the craving for tobacco or controlling tobacco withdrawal symptoms which comprises internally administering to said human an effective amount of an organic thio compound selected from the group thioglycerols, thioglycols or one of their pharmaceutically acceptable salts to control said craving or said withdrawal symptoms so as to reduce the desire for tobacco.

* * * * *